United States Patent [19]

Lindner et al.

[11] Patent Number: 4,996,208
[45] Date of Patent: Feb. 26, 1991

[54] PESTICIDAL THIAZOLOPYRIMIDINE DERIVATIVES

[75] Inventors: Werner Lindner, Cologne; Wilhelm Brandes, Leichlingen, both of Fed. Rep. of Germany

[73] Assignee: Bayer Aktiengesellschaft, Leverkusen, Fed. Rep. of Germany

[21] Appl. No.: 367,820

[22] Filed: Jun. 19, 1989

[30] Foreign Application Priority Data

Jun. 28, 1988 [DE] Fed. Rep. of Germany ....... 3821711

[51] Int. Cl.$^5$ .................. A61K 31/495; C07D 495/04
[52] U.S. Cl. .................................... 514/258; 544/278; 548/199
[58] Field of Search .................. 544/278; 514/258

[56] References Cited

U.S. PATENT DOCUMENTS 4,535,081  8/1985  Kadin et al. ....................... 514/258

FOREIGN PATENT DOCUMENTS 1193498  5/1965  Fed. Rep. of Germany .

OTHER PUBLICATIONS

J.A. Chem. Soc., 64, pp. 2709-2712 (1942).

Primary Examiner—Mukund J. Shah
Assistant Examiner—E. Bernhardt
Attorney, Agent, or Firm—Sprung Horn Kramer & Woods

[57] ABSTRACT

Fungicidal thiazolopyrimidine derivatives of the formula

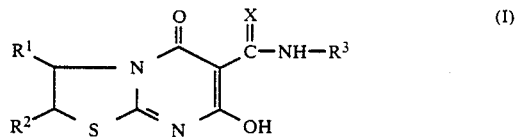

in which
$R^1$ stands for hydrogen or alkyl,
$R^2$ stands for hydrogen, alkyl or optionally substituted aryl,
$R^3$ stands in each case for optionally substituted alkyl, cycloalkyl, aryl, arylcarbonyl or arylsulphonyl, and
X stands for oxygen or sulphur.

9 Claims, No Drawings

PESTICIDAL THIAZOLOPYRIMIDINE DERIVATIVES

The present invention relates to novel thiazolopyrimidine derivatives, a process and novel intermediates for their preparation, and their use as pesticides.

Certain thiazolopyrimidine derivatives, such as, for example, 2,3,6,7-tetrahydro-5,7-dioxo-5-thiazolo-[3,2-a]-pyrimidine, are already known from the literature (cf. J. Am. Chem. Soc. 64 (1942), 2709–2712); however, nothing has previously been disclosed about the use of such compounds as pesticides.

On the other hand, for example N,N-dimethyl-N'-phenyl-(N'-fluorodichloromethylthio)-sulphamide (dichlofluanid/Euparen) is known as a pesticide, in particular for combating fungal plant diseases (cf. DE-AS (German Published Specification) 1,193,498).

Novel thiazolopyrimidine derivatives of the general formula (I)

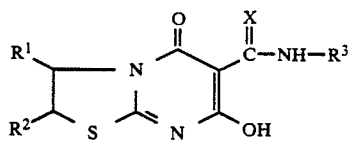

in which $R^1$ stands for hydrogen or alkyl, $R^2$ stands for hydrogen, alkyl or optionally substituted aryl, $R^3$ stands in each case for optionally substituted alkyl, cycloalkyl, aryl, arylcarbonyl or arylsulphonyl, and X stands for oxygen or sulphur have now been found.

The compounds of the formula (I) are in tautomeric equilibrium with compounds of the formula (IA) and IB):

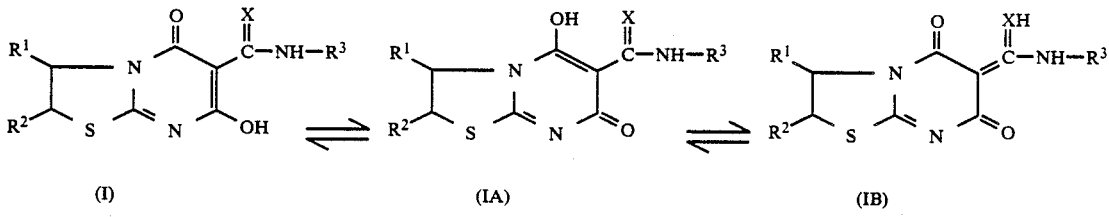

The discussions hereinbelow refer to compounds of formula (I) but they are intended to embrace both the pure compounds and the mixtures of the tautomeric structures.

Furthermore, il has been found that the novel compounds of the general formula (I)

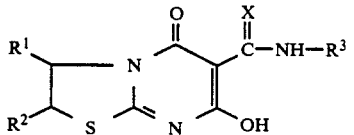

in which in which $R^1$ stands for hydrogen or alkyl, $R^2$ stands for hydrogen, alkyl or optionally substituted aryl, $R^3$ stands in each case for optionally substituted alkyl, cycloalkyl, aryl, arylcarbonyl or arylsulphonyl, and X stands for oxygen or sulphur are obtained when thiazolopyrimidines of the general formula (II)

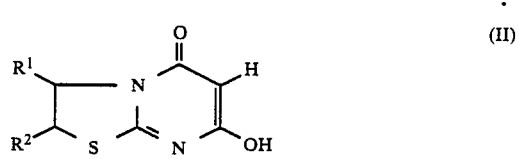

in which $R^1$ and $R^2$ have the abovementioned meanings, are reacted with iso(thio)cyanates of the general formula (III)

in which $R^3$ and X have the abovementioned meanings, if appropriate in the presence of an acid acceptor and if appropriate in the presence of a diluent.

The novel thiazolopyrimidine derivatives of the general formula (I) show a powerful action as pesticides, in particular as fungicides, and additionally, to a certain extent, as insecticides.

Surprisingly, the novel compounds of the formula (I) show a considerably more powerful action than N,N-dimethyl-N'-phenyl-(N'-fluorodichloromethylthio)-sulphamide, which is known.

In the general formulae, alkyl denotes straight-chain or branched alkyl preferably having 1 to 6, in particular 1 to 4, and particularly preferably 1 or 2, carbon atoms.

Cycloalkyl of the general formulae preferably contains 3 to 7, in particular 3, 5 or 6, ring members. Examples which may be mentioned are cyclopropyl, cyclopentyl and cyclohexyl.

Aryl of the general formulae preferably denotes phenyl or naphthyl, in particular phenyl. The aryl moieties in arylcarbonyl and arylsulphonyl are preferably naphthyl and phenyl, in particular phenyl.

The optionally substituted radicals of the general formulae can be substituted by one or more than one, preferably 1 to 3, identical or different substituents.

Preferred substituents which may be mentioned are: Halogen, cyano, nitro, alkoxycarbonyl having 1 to 4 carbon atoms in the alkoxy radical, phenyl, phenoxy [which is optionally substituted by a trifluoromethyl group and/or one to 3 halogen atoms], alkyl having 1 to 4 carbon atoms, halogenoalkyl having 1 or 2 carbon atoms and 1 to 5 identical or different halogen atoms, alkoxy having 1 to 4 carbon atoms, halogenoalkoxy having 1 or 2 carbon atoms and 1 to 5 identical or different halogen atoms, alkylthio having 1 to 4 carbon atoms, halogenoalkylthio having 1 or 2 carbon atoms and 1 to 5 identical or different halogen atoms, alkylsulphinyl having 1 to 4 carbon atoms, halogenoalkylsulphinyl having 1 or 2 carbon atoms and 1 to 5 identical or different halogen atoms, alkylsulphonyl having 1 to 4 carbon atoms, halogenoalkylsulphonyl having 1 or 2 carbon atoms and 1 to 5 identical or different halogen atoms or, in the case of phenyl, a benzo group or an alkanediyl group which has up to 4 carbon atoms, which is optionally interrupted once or twice by oxygen and/or a carbonyl group, and which is fused.

Unless stated otherwise, halogen denotes fluorine, chlorine, bromine or iodine, preferably fluorine, chlorine or bromine, and particularly preferably fluorine or chlorine.

In the general formulae, $R^1$ and $R^2$ preferably stand for hydrogen.

$R^3$ in the general formulae preferably denotes optionally substituted phenyl which may have 1 to 3 identical or different substituents from the series mentioned above. Particularly preferred substituents which may be mentioned are: halogen (preferably chlorine), nitro, $C_1$-$C_4$-alkyl (preferably methyl), $C_1$-$C_4$-alkoxy (preferably methoxy and ethoxy), $C_1$-$C_4$-halogenoalkyl (preferably trifluoromethyl), $C_1$-$C_4$-halogenoalkoxy (preferably trifluoromethoxy), $C_1$-$C_4$-halogenoalkylthio (preferably trifluoromethylthio and difluoro-chloro-methylthio), $C_1$-$C_4$-halogenoalkylsulphonyl (preferably trifluoromethylsulphonyl) or phenoxy which, in turn, can be substituted by the radicals mentioned above.

In the general formulae, X preferably stands for oxygen.

Formula (I) provides the general definition of the thiazolopyrimidine derivatives according to the invention. Preferred compounds of the formula (I) are those in which $R^1$ stands for hydrogen or for straight-chain or branched alkyl having 1 to 6 carbon atoms, $R^2$ stands for hydrogen, for straight-chain or branched alkyl having 1 to 6 carbon atoms or for phenyl which is optionally monosubstituted to trisubstituted by identical or different substituents from the series comprising halogen, cyano, nitro, alkyl having 1 to 4 carbon atoms, halogenoalkyl having 1 or 2 carbon atoms and 1 to 5 identical or different halogen atoms, alkoxy having 1 to 4 carbon atoms, halogenoalkoxy having 1 or 2 carbon atoms and 1 to 5 identical or different halogen atoms, alkylthio having 1 to 4 carbon atoms, halogenoalkylthio having 1 or 2 carbon atoms and 1 to 5 identical or different halogen atoms, alkylsulphinyl having 1 to 4 carbon atoms, halogenoalkylsulphinyl having 1 or 2 carbon atoms and 1 to 5 identical or different halogen atoms, alkylsulphonyl having 1 to 4 carbon atoms and/or halogenoalkylsulphonyl having 1 or 2 carbon atoms and 1 to 5 identical or different halogen atoms, $R^3$ stands for straight-chain or branched alkyl which has 1 to 6 carbon atoms and which is optionally substituted by halogen, cyano or slkoxycarbonyl having 1 to 4 carbon atoms in the alkoxy radical, for cycloalkyl which has 3 to 6 carbon atoms and which is optionally monosubstituted to trisubstituted by identical or different substituents from the series comprising halogen, cyano and/or alkoxycarbonyl having 1 to 4 carbon atoms in the alkoxy radical, or for phenyl, phenylcarbonyl or phenylsulphonyl, each of which is optionally monosubstituted to trisubstituted by identical or different substituents from the series comprising halogen, cyano, nitro, phenyl, phenoxy [which is optionally substituted by a trifluoromethyl group and/or one to 3 halogen atoms], alkyl having 1 to 4 carbon atoms, halogenoalkyl having 1 or 2 carbon atoms and 1 to 5 identical or different halogen atoms, alkoxy having 1 to 4 carbon atoms, halogenoalkoxy having 1 or 2 carbon atoms and 1 to 5 identical or different halogen atoms, alkylthio having 1 to 4 carbon atoms, halogenoalkylthio having 1 or 2 carbon atoms and 1 to 5 identical or different halogen atoms, alkylsulphinyl having 1 to 4 carbon atoms, halogenoalkylsulphinyl having 1 or 2 carbon atoms and 1 to 5 identical or different halogen atoms, alkylsulphonyl having 1 to 4 carbon atoms and/or halogenoalkylsulphonyl having 1 or 2 carbon atoms and 1 to 5 identical or different halogen atoms, or for phenyl which is fused to a benzo group or to an alkanediyl group which has up to 4 carbon atoms and which is optionally interrupted once or twice by oxygen and/or a carbonyl group, and X stands for oxygen or sulphur.

Particularly preferred compounds of the formula (I) are those in which $R^1$ stands for hydrogen, methyl, ethyl, propyl, isopropyl, butyl or isobutyl (preferably for hydrogen), $R^2$ stands for hydrogen, methyl, ethyl, propyl, isopropyl, butyl, isobutyl or phenyl which is optionally monosubstituted or disubstituted by identical or different substituents from the series comprising fluorine, chlorine, bromine, cyano, nitro, methyl, ethyl, trifluoromethyl, methoxy, ethoxy, difluoromethoxy, trifluoromethoxy, tetrafluoroethoxy, chlorotrifluoroethoxy, methylthio, ethylthio, trifluoromethylthio, methylsulphonyl and/or trifluoromethylsulphonyl, $R^3$ stands for cyclohexyl or for phenyl or phenylsulphonyl, the latter two (phenyl and phenylsulphonyl) in each case optionally being monosubstituted to trisubstituted by identical or different substituents from the series comprising fluorine, chlorine, bromine, cyano, nitro, phenyl, phenoxy [which is optionally substituted by a trifluoromethyl group and/or by 1 to 3 fluorine and/or chlorine atoms], methyl, ethyl, propyl, isopropyl, butyl, isobutyl, tert-butyl, trifluoromethyl, methoxy, ethoxy, propoxy, isopropoxy, difluoromethoxy, trifluoromethoxy, chlorodifluoromethoxy, tetrafluoroethoxy, chlorotrifluoroethoxy, methylthio, ethylthio, difluoromethylthio, trifluoromethylthio, chlorodifluoromethylthio, tetrafluoroethylthio, chlorotrifluoroethylthio, methylsulphinyl, ethylsulphinyl, trifluoromethylsulphinyl, methylsulphonyl, ethylsulphonyl and/or trifluoromethylsulpnonyl, or for phenyl which is fused to a benzo group or to 1,3-dioxa-propan-1,3-diyl (methylenedioxy), 1,4-dioxa-butan-1,4-diyl or 1,3-dioxabutan-1,4-diyl, and X stands for oxygen.

Very particularly preferred compounds of the formula (I) are those in which $R^1$ and $R^2$ stand for hydrogen, $R^3$ stands for phenyl which can be substituted by 1 or 2 identical or different radicals from the series comprising fluorine, chlorine, nitro, methyl, trifluoromethyl, methoxy, trifluoromethoxy, trifluoromethylthio and fluorochloromethylthio (preferably chlorine, methyl and trifluoromethoxy) and X stands for oxygen.

Examples of the compounds of the general formula (I), according to the invention, are listed in Table 1 below.

Table 1

Examples of the compounds of the formula (I) (in all examples, X stands for oxygen)

TABLE 1

$$\text{(I)}$$

Structure: R¹R²CH-CH(S)-N-C(=O)-C(=C(OH)-N=)-C(=X)-NH-R³ (thiazine-fused pyrimidine core)

| R¹ | R² | R³ |
|---|---|---|
| H | H | cyclohexyl |
| H | H | phenyl |
| H | H | —SO₂—phenyl |
| H | H | 2-F-phenyl |
| H | H | 3-F-phenyl |
| H | H | 2,4-di-F-phenyl |
| H | H | 3,4-di-F-phenyl |
| H | H | —SO₂—(2-F-phenyl) |
| H | H | 2-Cl-phenyl |
| H | H | 3-Cl-phenyl |

TABLE 1-continued

| R¹ | R² | R³ |
|---|---|---|
| H | H | 4-Cl-phenyl |
| H | H | 2,4-di-Cl-phenyl |
| H | H | 2,5-di-Cl-phenyl |
| H | H | 3,4-di-Cl-phenyl |
| H | H | 3,5-di-Cl-phenyl |
| H | H | 2-Br-phenyl |
| H | H | 4-Br-phenyl |
| H | H | 2,6-di-F-phenyl (with Cl) |
| H | H | 4-Cl-3-F-phenyl |

TABLE 1-continued (I)

Structure: R¹-CH(-CH(R²)-S-)N-C(=O)-C(=C(OH)-N=)-C(=X)-NH-R³ (thiazolidine-pyrimidine ring system)

| R¹ | R² | R³ |
|---|---|---|
| H | H | 2-methyl-4-chloro-5-fluorophenyl (Cl, F on phenyl) |
| H | H | —SO₂—(2-chlorophenyl) |
| H | H | —SO₂—(4-chlorophenyl) |
| H | H | —SO₂—(2,4-dichlorophenyl) |
| H | H | —SO₂—(2,5-dichlorophenyl) |
| H | H | —SO₂—(2-bromophenyl) |
| H | H | —SO₂—(4-bromophenyl) |
| H | H | —SO₂—(4-chloro-2-fluorophenyl) |
| H | H | 4-nitrophenyl |
| H | H | 4-cyanophenyl |
| H | H | 4-biphenylyl |
| H | H | 4-phenoxyphenyl |
| H | H | 4-(4-chlorophenoxy)phenyl |
| H | H | 4-(2,4-dichlorophenoxy)phenyl |
| H | H | 4-(4-trifluoromethylphenoxy)phenyl |
| H | H | 4-(3-trifluoromethylphenoxy)phenyl |
| H | H | 4-(2-chloro-4-trifluoromethylphenoxy)phenyl |
| H | H | 4-(2-chloro-6-fluoro-4-trifluoromethylphenoxy)phenyl |
| H | H | 2-methylphenyl |
| H | H | 3-methylphenyl |

TABLE 1-continued $$(I)$$

Structure: R¹R²CH-CH(S)-N-C(=N)-C(=O)-C(=C-OH)-C(=X)-NH-R³ (thiazoline fused pyrimidine core)

| R¹ | R² | R³ |
|---|---|---|
| H | H | 4-methylphenyl (–C₆H₄–CH₃) |
| H | H | 2,4-dimethylphenyl |
| H | H | 2,4-dimethylphenyl (CH₃ at different position) |
| H | H | 4-ethylphenyl (–C₆H₄–C₂H₅) |
| H | H | 2-CF₃-phenyl |
| H | H | 3-CF₃-phenyl |
| H | H | 4-CF₃-phenyl |
| H | H | 3,5-bis(CF₃)phenyl |
| H | H | –SO₂–(2-CH₃-phenyl) |
| H | H | –SO₂–(4-CH₃-phenyl) |
| H | H | –SO₂–(2-CF₃-phenyl) |
| H | H | –SO₂–(4-CF₃-phenyl) |
| H | H | 4-OCH₃-phenyl |
| H | H | 3-OCH₃-phenyl |
| H | H | 3,4-di-OCH₃-phenyl |
| H | H | 4-OC₂H₅-phenyl |
| H | H | 3-OC₂H₅-phenyl |
| H | H | 2-OCHF₂-phenyl |
| H | H | 4-OCHF₂-phenyl |
| H | H | 3-OCF₃-phenyl |

TABLE 1-continued (I) Structure with R¹, R², R³, X substituents on thiazoline-fused pyrimidine ring system.

| R¹ | R² | R³ |
|---|---|---|
| H | H | -C₆H₄-OCF₃ (para) |
| H | H | -C₆H₃(Cl)-OCF₃ (3-Cl, 4-OCF₃) |
| H | H | -C₆H₃(Cl)-OCF₃ |
| H | H | -C₆H₃(Cl)-CF₃ |
| H | H | -SO₂-C₆H₄-OCHF₂ (ortho) |
| H | H | -SO₂-C₆H₄-OCHF₂ (para) |
| H | H | -SO₂-C₆H₄-OCF₃ (ortho) |
| H | H | -SO₂-C₆H₄-OCF₃ (para) |
| H | H | -C₆H₄-OCF₂Cl |
| H | H | -C₆H₄-OCF₂CHF₂ |
| H | H | -C₆H₄-OCF₂CF₂Cl |
| H | H | -C₆H₄-SCH₃ |
| H | H | -C₆H₄-SC₂H₅ |
| H | H | -C₆H₃(Cl)-SCH₃ |
| H | H | -C₆H₄-SO-CH₃ |
| H | H | -C₆H₄-SO-CF₃ |
| H | H | -C₆H₄-SO₂CH₃ |
| H | H | -C₆H₄-SO₂CF₃ |
| H | H | 1-naphthyl |
| H | H | benzo[1,3]dioxol-5-yl |
| H | H | 2,3-dihydro-1,4-benzodioxin-6-yl |

TABLE 1-continued $$\text{(I)}$$

Structure: R¹, R² on carbon attached to S and N of a 6-membered ring containing S, C(=N), N, C(=O), C (bearing C(=X)NH-R³), C-OH.

| R¹ | R² | R³ |
|---|---|---|
| H | H | 2-(methylenedioxymethyl)-5-methylphenyl (benzodioxole derivative) |
| CH₃ | phenyl | 4-Cl-phenyl |
| CH₃ | phenyl | 4-OCF₃-phenyl |
| CH₃ | phenyl | 4-CF₃-phenyl |
| CH₃ | phenyl | 4-CH₃-phenyl |
| CH₃ | phenyl | 4-OCH₃-phenyl |
| CH₃ | phenyl | 2-Cl-phenyl |
| CH₃ | phenyl | 2-CH₃-phenyl |
| CH₃ | phenyl | 2-OCH₃-phenyl |
| CH₃ | phenyl | 2-CF₃-phenyl |
| CH₃ | phenyl | 2-NO₂-phenyl |
| CH₃ | phenyl | 2,4-di-Cl-phenyl |
| CH₃ | phenyl | 2-CH₃-4-Cl-phenyl |
| CH₃ | phenyl | 2,4-di-CH₃-phenyl |
| CH₃ | phenyl | 3-Cl-phenyl |
| CH₃ | phenyl | 3-CH₃-phenyl |
| CH₃ | phenyl | phenyl |
| H | phenyl | phenyl |
| H | phenyl | 2,3-di-Cl-phenyl |
| H | phenyl | 3-Cl-phenyl |

TABLE 1-continued

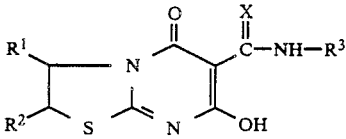

| R¹ | R² | R³ |
|---|---|---|
| H | 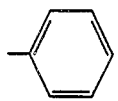 | 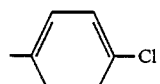 |
| H | 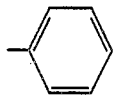 | 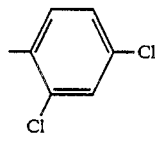 |
| H | 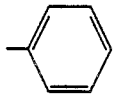 | 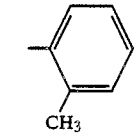 |
| H | 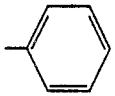 | 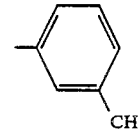 |
| H | 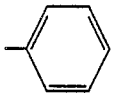 | 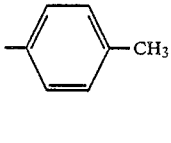 |
| H |  | 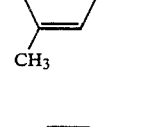 |
| H | 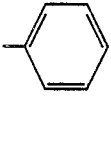 | 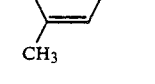 |
| H | 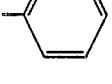 | 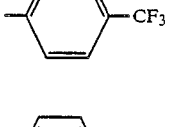 |
| H | 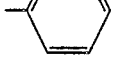 | 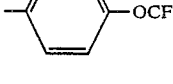 |

TABLE 1-continued

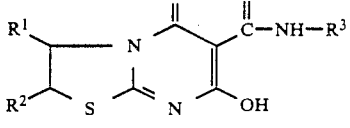

| R¹ | R² | R³ |
|---|---|---|
| H | 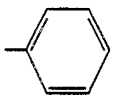 | 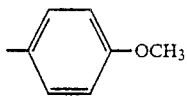 |
| H | 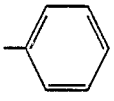 | 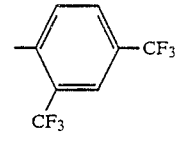 |
| H | 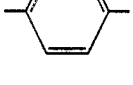 | 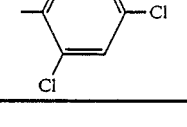 |

If, for example, 2,3,6,7-tetrahydro-5,7-dioxo-5-thiazolo-[3,2-a]-pyrimidine and phenyl isocyanate are used as starting substances, the course of the reaction in the preparation process according to the invention can be represented by the following equation:

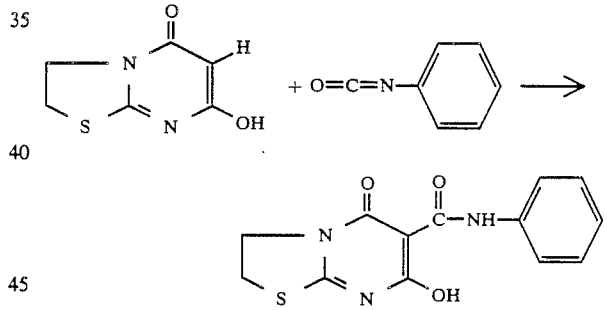

Formula (II) provides a general definition of the thiazolopyrimidines to be used as starting substances in the process according to the invention for the preparation of compounds of the formula (I).

In formula (II), $R^1$ and $R^2$ preferably, or in particular, have those meanings which have already been mentioned above in connection with the description of the compounds of the formula (I), according to the invention, as being preferred, or particularly preferred, for $R^1$ and $R^2$.

Examples of the starting substances of the formula (II) are listed in Table 2 below.

Table 2

Examples of the starting substances of the formula (II)

TABLE 2

Examples of the starting substances of the formula (II)

(II) — structure of formula II with R¹, R² on thiazolidine fused to pyrimidine bearing =O, H, OH, N.

| R¹ | R² | R¹ | R² | R¹ | R² |
|---|---|---|---|---|---|
| H | H | H | 4-F-C₆H₄– | CH₃ | 4-CF₃-C₆H₄– |
| CH₃ | CH₃ | | | | |
| CH₃ | H | H | 4-Cl-C₆H₄– | CH₃ | 4-OCH₃-C₆H₄– |
| H | CH₃ | | | | |
| C₂H₅ | H | H | 4-CH₃-C₆H₄– | | |
| C₃H₇ | H | | | | |
| C₂H₅ | CH₃ | H | 4-CF₃-C₆H₄– | | |
| C₃H₇ | CH₃ | | | | |
| CH₃ | C₂H₅ | H | 4-OCH₃-C₆H₄– | | |
| CH₃ | C₃H₇ | | | | |
| H | C₂H₅ | CH₃ | C₆H₅– | | |
| H | C₃H₇ | | | | |
| H | C₆H₅– | CH₃ | 4-F-C₆H₄– | | |
| CH₃ | C₆H₅– | CH₃ | 4-Cl-C₆H₄– | | |
| C₂H₅ | C₆H₅– | CH₃ | 4-CH₃-C₆H₄– | | |

With the exception of 2,3,6,7-tetrahydro-5,7-dioxo-5-thiazolo-[3,2-a]-pyrimidine (I, $R^1=R^2=H$), the starting substances of the formula (II) are novel and part of the present invention.

The novel thiazolopyrimidines of the formula (II) are obtained when iminothiazolidines of the general formula (IV)

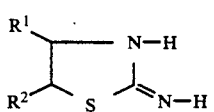

(IV)

in which $R^1$ and $R^2$ have the abovementioned meanings, are reacted with malonic acid esters, such as, for example, dimethyl malonate or diethyl malonate, in the presence of metals, metal hydroxides and/or metal alkoxides, such as, for example, sodium, sodium hydroxide, sodium methoxide and/or sodium ethoxide, in the presence of diluents, such as, for example, methanol and/or ethanol, at temperatures between 10° C. and 100° C.

In formula (IV), $R^1$ and $R^2$ preferably, or in particular, have those meanings which have already been mentioned above in connection with the description of the compounds of the formula (I), according to the invention, as being preferred, or particularly preferred, for $R^1$ and $R^2$.

Examples of the compounds of the formula (IV) which may be mentioned are: 2-imino-4-methyl-thiazolidine, 2-imino-5-methyl-thiazolidine, 2-imino-4,5-dimethyl-thiazolidine, 2-imino-4-ethylthiazolidine, 2-imino-5-ethyl-thiazolidine, 2-imino-5-phenyl-thiazolidine, 2-imino-4-methyl-5-phenyl-thiazolidine and 2-imino-4-ethyl-5-phenyl-thiazolidine.

The compounds of the formula (IV) are known and/or can be prepared by processes known per se (cf. J. Am. Chem. Soc. 80 (1958), 3342; Chem. Abstracts 78 (1973), 43477p; Chem. Abstracts 100 (1984), 85726x).

Formula (III) provides a general definition of the iso(thio)cyanates also to be used as starting substances in the process according to the invention.

In formula (III), $R^3$ and X preferably, or in particular, have those meanings which have already been mentioned above in connection with the compounds of the formula (I), according to the invention, as being preferred, or particularly preferred, for $R^3$ and X.

Examples of the starting substances of the formula (III) which may be mentioned are: cyclohexyl isocyanate, phenyl isocyanate, phenylsulphonyl isocyanate, 2-fluoro-phenyl isocyanate, 2-fluoro-phenylsulphonyl isocyanate, 3-fluoro-phenyl isocyanate, 3-fluorophenylsulphonyl isocyanate, 4-fluoro-phenyl isocyanate, 4-fluoro-phenylsulphonyl isocyanate, 2,4-difluoro-phenyl isocyanate, 2,4-difluoro-phenylsulphonyl isocyanate, 3,4-difluoro-phenyl isocyanate, 3,4-difluoro-phenylsulphonyl isocyanate, 2-chloro-phenyl isocyanate, 2-chloro-phenylsulphonyl isocyanate, 3-chloro-phenyl isocyanate, 3-chlorophenylsulphonyl isocyanate, 4-chloro-phenyl isocyanate, 4-chloro-phenylsulphonyl isocyanate, 2,4-dichlorophenyl isocyanate, 2,4-dichloro-phenylsulphonyl isocyanate, 2,5-dichloro-phenyl isocyanate, 2,5-dichlorophenylsulphonyl isocyanate, 3,4-dichloro-phenyl isocyanate, 3,4-dichloro-phenylsulphonyl isocyanate, 3,5-dichloro-phenyl isocyanate, 3,5-dichloro-phenylsulphonyl isocyanate, 2-bromo-phenyl isocyanate, 2-bromo-phenylsulphonyl isocyanate, 3-bromo-phenyl isocyanate, 3-bromo-phenylsulphonyl isocyanate, 4-bromo-phenyl isocyanate, 4-bromo-phenylsulphonyl isccyanate, 2-methyl-phenyl isocyanate, 2-methyl-phenylsulphonyl isocyanate, 3-methyl-phenyl isocyanate, 3-methyl-phenylsulphonyl isocyanate, 4-methyl-phenyl isocyanate, 4-methyl-phenylsulphonyl isocyanate, 2,4-dimethyl-phenyl isocyanate, 3,4-dimethyl-phenyl isocyanate, 4-ethyl-phenyl isocyanate, 2-trifluoromethyl-phenyl isocyanate, 2-trifluoromethylphenylsulphonyl isocyanate, 3-trifluoromethyl-phenyl isocyanate, 3-trifluoromethylphenylsulphonyl isocyanate, 4-trifluoromethyl-phenyl isocyanate, 4-trifluoromethylphenylsulphonyl isocyanate, 2-methoxyphenyl isocyanate, 2-methoxy-phenylsulphonyl isocyanate, 3-methoxy-phenyl isocyanate, 3-methoxy-phenylsulphonyl isocyanate, 4-methoxyphenyl isocyanate, 4-methoxy-phenylsulphonyl isocyanate, 2-difluoromethoxy-phenyl isocyanate, 2-difluoromethoxy-phenylsulphonyl isocyanate, 4-difluoromethoxy-phenyl isocyanate, 4-difluoromethoxy-phenylsulphonyl isocyanate, 2-trifluoromethoxy-phenyl isocyanate, 2-trifluoromethoxy-phenylsulphonyl isocyanate, 3-trifluoromethoxy-phenyl isocyanate, 3-trifluoromethoxy-phenylsulphonyl isocyanate, 4-trifluoromethoxy-phenyl isocyanate, 4-trifluoromethoxy-phenylsulphonyl isocyanate 4-methylthio-phenyl isocyanate, 4-ethylthio-phenyl isocyanate, 1-naphthyl isocyanate, 2-naphthyl isocyanate and 4-methylenedioxy-phenyl isocyanate.

The starting substances of the formula (III) are known and/or can be prepared by processes known per se (cf. U.S. Pat. No. 4,732,711).

The process according to the invention for the preparation of the novel thiazolopyrimidine derivatives of the formula (I) is preferably carried out using diluents. Suitable diluents in this process are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in the process according to the invention are all acid-binding agents which can customarily be used for reactions of this type. Aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo[2,2,2]-octane (DABCO) are preferably suitable.

In the process according to the invention, the reaction temperatures can be varied within a relatively wide range. In general, the process is carried at temperatures between 0° C. and 100° C., preferably at temperatures between 10° C. and 50° C.

In general, the process according to the invention is carried out under atmospheric pressure. However, it is also possible to carry out the reaction under increased or reduced pressure.

For carrying out the process according to the invention, the starting substances required in each case are generally employed in approximately equimolar amounts. However, it is also possible to use one of the two components employed in each case in a relatively large excess. In general, the reactions are carried out in a suitable diluent in the presence of an acid acceptor, and the reaction mixture is stirred for several hours at the specific temperature required. In the process according to the invention, working up is carried out in each case by customary methods.

The reactive compounds according to the invention have a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, Xanthomonas campestris pv. oryzae; Pseudomonas species, such as, for example, Pseudomonas syringae pv. lachrymans; Erwinia species, such as, for example, Erwinia amylovora; Pythium species, such as, for example, Pythium ultimum; Phytophthora species, such as, for example, Phytophthora infestans; Pseudoperonospora species, such as, for example, Pseudoperonospora humuli or Pseudoperonospora cubensis; Plasmopara species, such as, for example, Plasmopara viticola; Peronospora species, such as, for example, Peronospora pisi or P. brassicae; Erysiphe species, such as, for example, Erysiphe graminis; Sphaerotheca species, such as, for example, Sphaerotheca fuliginea; Podosphaera species, such as, for example, Podosphaera leucotricha; Venturia species, such as, for example, Venturia inaequalis; Pyrenophora species, such as, for example, Pyrenophora teres or P. graminea (conidia form: Drechslera, syn: Helminthosporium); Cochliobolus species, such as, for example, Cochliobolus sativus (conidia form: Drechslera, syn: Helminthosporium); Uromyces Species, such as, for example, Uromyces appendiculatus; Puccinia species, such as, for example, Puccinia recondita; Tilletia species, such as, for example, Tilletia caries; Ustilago species, such as, for example, Ustilago nuda or Ustilago avenae; Pellicularia species, such as, for example, Pellicularia sasakii; Pyricularia species, such as, for example, Pyricularia oryzae; Fusarium species, such as, for example, Fusarium culmorum; Botrytis species, such as, for example, Botrytis cinerea; Septoria species, such as, for example, Septoria nodorum; Leptosphaeria species, such as, for example, Leptosphaeria nodorum; Cercospora species, such as, for example, Cercospora canescens; Alternaria species, such as, for example, Alternaria brassicae and Pseudocercosporella species, such as, for example, Pseudocercosporella herpotrichoides.

The good toleration, by plants, of the active compounds, at the concentrations required for combating plant diseases, permits treatment of above-ground parts of plants, of vegetative propagation stock and seeds, and of the soil.

In particular, the compounds of the formula (I) according to the invention show a powerful protective action against Plasmopara species, such as, for example, Plasmopara viticola on vines and against Botrytis species, such as, for example, Botrytis cinerea on beans. A good action can also be observed against Pyricularia oryzae on rice.

To a certain extent, animal pests, such as, for example, the larvae of beetles and mosquitoes, are also controlled.

Depending on their specific physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable for example ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable for example crushed and fractionated natural minerals such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products. As dispersing agents there are suitable for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

For the treatment of parts of plants, the active compound concentrations in the use forms can be varied within a substantial range. They are, in general, between 1 and 0.0001% by weight, preferably between 0.5 and 0.001%.

For the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

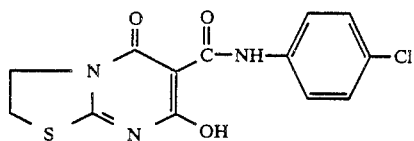

66 ml (0.44 mol) of 1,8-diazabicyclo-[5,4,0]-undec-7-ene (DBU) are added at 20° C. to 30° C. to a stirred mixture of 74 g (0.44 mol) of 2,3,6,7-tetrahydro-5,7-dioxo-5-thiazolo-[3,2-a]-pyrimidine, 67 g (0.44 mol) of 4-chlorophenyl isocyanate and 1000 ml of tetrahydrofuran, and the reaction mixture is stirred for another 60 minutes. It is then slowly diluted with water to approximately twice the volume, stirred for 15 more minutes and filtered. The filtrate is acidified using conc. hydrochloric acid, and the product obtained during this process in the form of crystals is isolated by filtration with suction.

130 g (91 % of theory) of 6-(4-chlorophenylaminocarbonyl)-2,3,6,7-tetrahydro-5,7-dioxo-5-thiazolo-[3,2-a]-pyrimidine of melting point 260° C. are obtained.

The compounds of the formula (I) listed in Table 3 below can be prepared in analogy to Example 1.

Table 3

Preparation examples of the compounds of the formula (I)

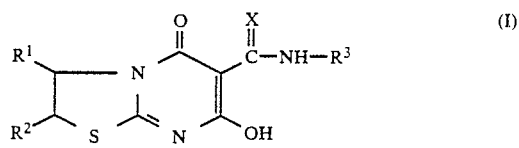

TABLE 3

| Ex. No. | $R^1$ | $R^2$ | $R^3$ | X | Melting point (°C.) |
|---|---|---|---|---|---|
| 2 | H | H | —⟨phenyl⟩—OCF$_3$ | O | 211 |
| 3 | H | H | —⟨phenyl⟩ with CF$_3$, CF$_3$ (3,5) | O | 221 |
| 4 | H | H | —⟨phenyl⟩ with CF$_3$, Cl | O | 269 |
| 5 | H | H | —⟨phenyl⟩—CF$_3$ | O | 267 |
| 6 | H | H | —⟨phenyl⟩ with NO$_2$, CF$_3$ | O | 272 |
| 7 | H | H | —⟨phenyl⟩—CH$_3$ | O | 275 |
| 8 | H | H | —⟨phenyl⟩—OC$_2$H$_5$ | O | 221 |

TABLE 3-continued
| Ex. No. | R¹ | R² | R³ | X | Melting point (°C.) |
|---|---|---|---|---|---|
| 9 | H | H | 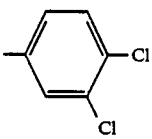 | O | 303 |
| 10 | H | H | 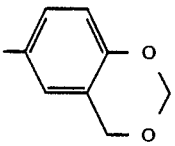 | O | 234 |
| 11 | H | H | 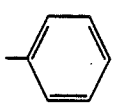 | O | 208 |
| 12 | H | H | 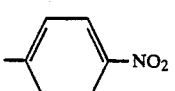 | O | 286 |
| 13 | H | H | 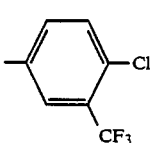 | O | 256 |
| 14 | H | H | 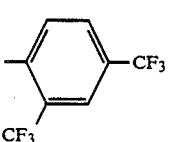 | O | 244 |
| 15 | H | H | 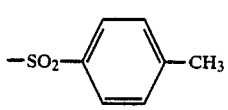 | O | 246 |
| 16 | H | H | 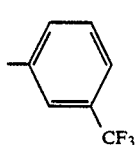 | O | 105 |
| 17 | H | H | 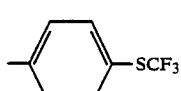 | O | 220 |
| 18 | H | H | 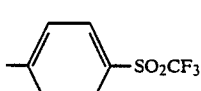 | O | 230 |
| 19 | H | H | 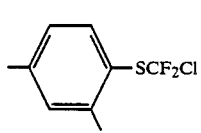 | O | 211 |

TABLE 3-continued

| Ex. No. | R¹ | R² | R³ | X | Melting point (°C.) |
|---|---|---|---|---|---|
| 20 | H | H | 2-Cl, 4-(SCF₃)-phenyl (SCF₃ at position, Cl at position) — phenyl with Cl and SCF₃ | O | 220 |
| 21 | H | H | phenyl with Cl and OCF₃ | O | 209 |
| 22 | H | H | phenyl with CH₃ | O | 257 |
| 23 | H | H | cyclohexyl (H) | O | 145 |
| 24 | H | H | phenyl with NO₂ | O | 228 |
| 25 | H | H | naphthyl | O | 253 |
| 26 | H | H | phenyl with Cl | O | 258 |
| 27 | H | H | phenyl-O-phenyl with CF₃ | O | 219 |
| 28 | H | H | phenyl with 2 Cl | O | 228 |
| 29 | H | H | phenyl with OCH₃ | O | 270 |

TABLE 3-continued
| Ex. No. | R¹ | R² | R³ | X | Melting point (°C.) |
|---|---|---|---|---|---|
| 30 | H | H | 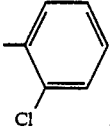 | O | 250 |
| 31 | H | H | 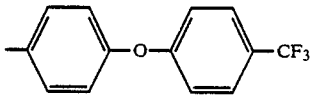 | O | 239 |
| 32 | H | H | 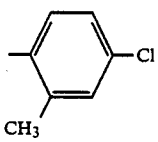 | O | 248 |
| 33 | H | H | 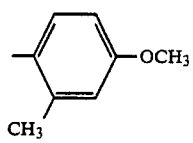 | O | 234 |
| 34 | H | H | 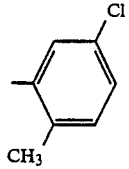 | O | 297 |
| 35 | H | H | 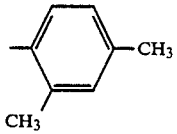 | O | 260 |
| 36 | CH₃ | C₆H₅ | 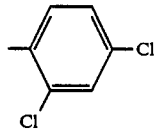 | O | 183 |
| 37 | CH₃ | C₆H₅ | 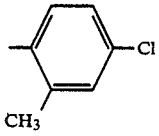 | O | 191 |
| 38 | CH₃ | C₆H₅ | 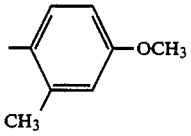 | O | 173 |
| 39 | CH₃ | C₆H₅ | 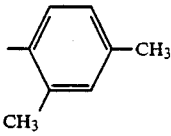 | O | 182 |

TABLE 3-continued
| Ex. No. | R¹ | R² | R³ | X | Melting point (°C.) |
|---|---|---|---|---|---|
| 40 | CH₃ | C₆H₅ | 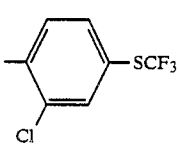 | O | 228 |
| 41 | CH₃ | C₆H₅ | 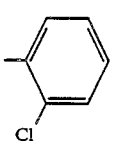 | O | 205 |
| 42 | CH₃ | C₆H₅ | 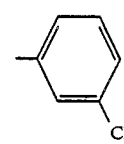 | O | 180 |
| 43 | CH₃ | C₆H₅ | 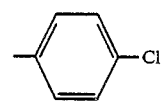 | O | 175 |
| 44 | CH₃ | C₆H₅ | 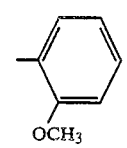 | O | 210 |
| 45 | CH₃ | C₆H₅ | 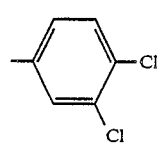 | O | 186 |
| 46 | CH₃ | C₆H₅ | 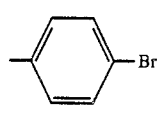 | O | 199 |
| 47 | CH₃ | C₆H₅ | 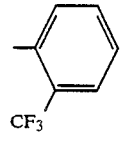 | O | 186 |
| 48 | CH₃ | C₆H₅ | 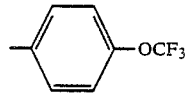 | O | 180 |
| 49 | CH₃ | C₆H₅ | 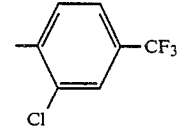 | O | 191 |
| 50 | CH₃ | C₆H₅ | 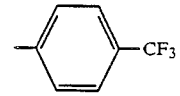 | O | 206 |

TABLE 3-continued

| Ex. No. | R¹ | R² | R³ | X | Melting point (°C.) |
|---|---|---|---|---|---|
| 51 | CH₃ | C₆H₅ | 3-Cl, 4-OCF₃-phenyl | O | 175 |
| 52 | CH₃ | C₆H₅ | 4-SCF₃-phenyl | O | 200 |
| 53 | CH₃ | C₆H₅ | 3,5-Cl₂-4-SCF₃-phenyl | O | 160 |
| 54 | CH₃ | C₆H₅ | 4-OCF₃-phenyl | O | 150 |
| 55 | CH₃ | C₆H₅ | 3,5-Cl₂-4-CF₃-phenyl | O | 233 |
| 56 | CH₃ | C₆H₅ | 3-Cl, 4-CF₃-phenyl | O | 178 |

STARTING SUBSTANCES OF THE FORMULA (II)

Example (II-1)

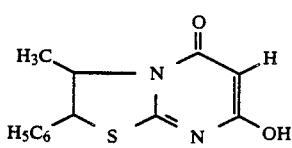

8.4 g (0.37 mol) of sodium are added to 200 ml of ethanol and, when the reaction is complete, 59 g (0.37 mol) of diethyl malonate and a solution of 70 g (0.37 mol) of 2-imino-4-methyl-5-phenyl-thiazolidine in 400 ml of ethanol are added in succession. The reaction mixture is stirred at 50° C. for one hour and under reflux for 12 more hours. The mixture is cooled using ice, then acidified using conc. hydrochloric acid and slowly diluted further with water. The product which precipitates in the form of crystals in this process is isolated by filtering off with suction.

72 g (76 % of theory) of 2-phenyl-3-methyl-2,3,6,7-tetrahydro-5,7-dioxo-5-thiazolo-[3,2-a]-pyrimidine of melting point 244° C. are obtained.

USE EXAMPLES

Example A

Plasmopara test (vines)/protective
Solvent:4.7 parts by weight of acetone
Emulsifier:0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100 % relative atmospheric humidity for 1 day. The plants are then placed in a greenhouse at 22° C. and about 80 % atmospheric humidity for 5 days. The plants are then moistened and placed in a humidity chamber for 1 day.

Evaluation is carried out 7 days after the inoculation.

In this test, for example the compound from Example 2 showed a degree of action of more than 90 % at an exemplary concentration of 5 ppm.

Example B

Botrytis test (been)/protective
Solvent:4.7 parts by weight of acetone
Emulsifier:0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of aar covered with otrytis cinerea are placed on each leaf. The inoculated plants are placed in a darkened humid chamber at 20° C. 3 days after the inoculation, the size of the lesions on the leaves is evaluated.

In this test, for example the compounds from Examples 28 and 32 showed a degree of action of more than 80 % at an exemplary concentration of 100 ppm.

It will be appreciated that the instant specification and claims are set forth by way of illustration and not limitation, and that various modifications and changes may be made without departing from the spirit and scope of the present invention.

What is claimed:

1. A thiazolopyrimidine derivative of the formula

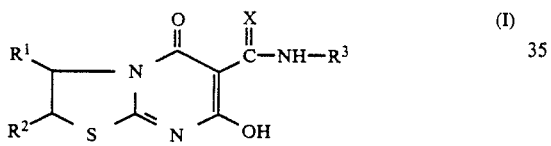

in which
R$^1$ stands for hydrogen or for straight-chain or branched alkyl having 1 to 6 carbon atoms,
R$^2$ stands for hydrogen, for straight-chain or branched alkyl having 1 to 6 carbon atoms or for phenyl which is optionally monosubstituted to trisubstituted by identical or different substituents from the group consisting of halogen, cyano, nitro, alkyl having 1 to 4 carbon atoms, halogenoalkyl having 1 or 2 carbon atoms and 1 to 5 identical or different halogen atoms, alkoxy having 1 to 4 carbon atoms, halogenoalkoxy having 1 or 2 carbon atoms and 1 to 5 identical or different halogen atoms, alkylthio having 1 to 4 carbon atoms, halogenoalkylthio having 1 or 2 carbon atoms and 1 to 5 identical or different halogen atoms, alkylsulphinyl having 1 to 4 carbon atoms, halogenoalkylsulphinyl having 1 or 2 carbon atoms and 1 to 5 identical or different halogen atoms, alkylsulphonyl having 1 to 4 carbon atoms and halogenoalkylsulphonyl having 1 or 2 carbon atoms and 1 to 5 identical or different halogen atoms,
R$^3$ stands for straight-chain or branched alkyl which has 1 to 6 carbon atoms and which is optionally substituted by halogen, cyano or alkoxycarbonyl having 1 to 4 carbon atoms in the alkoxy radical, for cycloalkyl which has 3 to 6 carbon atoms and which is optionally monosubstituted to trisubstituted by identical or different substituents from the group consisting of halogen, cyano and alkoxycarbonyl having 1 to 4 carbon atoms in the alkoxy radical, or for phenyl, phenylcarbonyl or phenylsulphonyl each of which is optionally monosubstituted to trisubstituted by identical or different substituents from the group consisting of halogen, cyano, nitro, phenyl, phenoxy (which is optionally substituted by a trifluoromethyl group and/or one to 3 halogen atoms), alkyl having 1 to 4 carbon atoms, halogenoalkyl having 1 or 2 carbon atoms and 1 to 5 identical or different halogen atoms, alkoxy having 1 to 4 carbon atoms, halogenoalkoxy having 1 or 2 carbon atoms and 1 to 5 identical or different halogen atoms, alkylthio having 1 to 4 carbon atoms, halogenoalkylthio having 1 or 2 carbon atoms and 1 to 5 identical or different halogen atoms, alkylsulphinyl having 1 to 4 carbon atoms, halogenoalkylsulphinyl having 1 or 2 carbon atoms and 1 to 5 identical or different halogen atoms, alkylsulphonyl having 1 to 4 carbon atoms and/or halogenoalkylsulphonyl having 1 or 2 carbon atoms and 1 to 5 identical or different halogen atoms, or for phenyl which is fused to a benzo group or to an alkanediyl group which has up to 4 carbon atoms and which is optionally interrupted once or twice by oxygen and/or a carbonyl group, and X stands for oxygen or sulphur.

2. A thiazolopyrimidine derivative according to claim 1, in which
R$^1$ stands for hydrogen, methyl, ethyl, propyl, isopropyl, butyl or isobutyl,
R$^2$ stands for hydrogen, methyl, ethyl, propyl, isopropyl, butyl, isobutyl or phenyl which is optionally monosubstituted or disubstituted by identical or different substituents from the group consisting of fluorine, chlorine, bromine, cyano, nitro, methyl, ethyl, trifluoromethyl, methoxy, ethoxy, difluoromethoxy, trifluoromethoxy, tetrafluoroethoxy, chlorotrifluoroethoxy, methylthio, ethylthio, trifluoromethylthio, methylsulphonyl and trifluoromethylsulphonyl,
R$^3$ stands for cyclohexyl; for phenyl or phenylsulphonyl each optionally monosubstituted to trisubstituted by identical or different substituents from the group consisting of fluorine, chlorine, bromine, cyano, nitro, phenyl, phenoxy (which is optionally substituted by a trifluoromethyl group and/or by 1 to 3 fluorine and/or chlorine atoms), methyl, ethyl, propyl, isopropyl, butyl, isobutyl, tert-butyl, trifluoromethyl, methoxy, ethoxy, propoxy, isopropoxy, difluoromethoxy, trifluoromethoxy, chlorodifluoromethoxy, tetrafluoroethoxy, chlorotrifluoroethoxy, methylthio, ethylthio, difluoromethylthio, trifluoromethylthio, chlorodifluoromethylthio, tetrafluoroethylthio, chlorotrifluoroethylthio, methylsulphinyl, ethylsulphinyl, trifluoromethylsulphinyl, methylsulphonyl, ethylsulphonyl and trifluoromethylsulphonyl; or for phenyl which is fused to a benzo group or to 1,3-dioxa-propan-1,3-diyl (methylenedioxy), 1,4-dioxa-butan-1,4-diyl or 1,3-dioxa-butan-1,4-diyl, and X stands for oxygen.

3. A thiazolopyrimidina derivative according to claim 1 in which,
R$^1$ and R$^2$ stand for hydrogen, and
R$^3$ stands for phenyl which is optionally monosubstituted or disubstituted by identical or different substituents from the group consisting of fluorine, chlorine, nitro, methyl, trifluoromethyl, methoxy, trifluoromethoxy, trifluoromethylthio and fluorochloromethylthio, and X stands for oxygen.

4. A compound according to claim 1, wherein such compound is 6-(4-trifluoromethoxy-phenylamino-carbonyl)-2,3,6,7-tetrahydro-5,7-dioxo-5-triazolo-[3,2-a]-pyrimidine of the formula

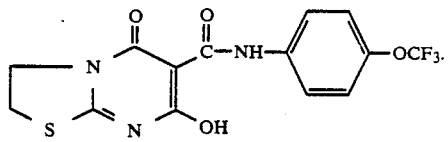

5. A compound according to claim 1, wherein such compound is 6-(2,4-dichloro-phenylamino-carbonyl)-2,3,6,7-tetrahydro-5,7-dioxo-5-thiazolo-[3,2-a]-pyrimidine of the formula

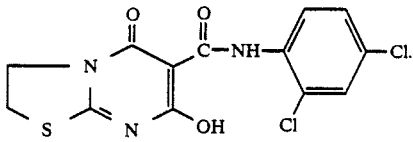

6. A compound according to claim 1, wherein such compound is 6-(4-chloro-2-methyl-phenylamino-carbonyl)-2,3,6,7-tetrahydro-5,7-dioxo-5-thiazolo-[3,2-a]-pyrimidine of the formula

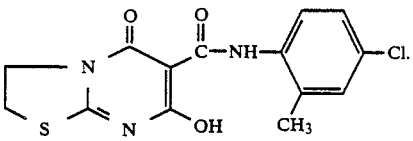

7. A fungicidal composition comprising a fungicidally effective amount of a compound according to claim 1 and a diluent.

8. A method of combating fungi which comprises applying to such fungi or to a fungus habitat a fungicidally effective amount of a compound according to claim 1.

9. The method according to claim 8 wherein such compound is
6-(4-trifluoromethoxy-phenylamino-carbonyl)-2,3,6,7-tetrahydro-5,7-dioxo-5-thiazolo-[3,2-a]-pyrimidine,
6-(2,4-dichloro-phenylamino-carbonyl)-2,3,6,7-tetrahydro-5,7-dioxo-5-thiazolo-[3,2-a]-pyrimidine, or
6-(4-chloro-2-methyl-phenylamino-carbonyl)-2,3,6,7-tetrahydro-5,7-dioxo-5-thiazolo-[3,2-a]-pyrimidine.

* * * * *